United States Patent [19]

Ceccarelli et al.

[11] Patent Number: 5,571,906

[45] Date of Patent: Nov. 5, 1996

[54] **PROCESS FOR OBTAINING OCTAHYDRO TRISODIUM SALT OF FRUCTOSE 1,6-DIPHOSPHATE (FDPNA3H*8H2O) IN CRYSTALLINE FORM**

[75] Inventors: Stefano Ceccarelli, Frosinone; Magnante Francesco, Colleferro; Zanarella Sergio, Mentana, all of Italy

[73] Assignee: Biomedica Foscama Industrial Chimico-Farmaceutica, S.p.A., Rome, Italy

[21] Appl. No.: 510,871

[22] Filed: Aug. 3, 1995

Related U.S. Application Data

[63] Continuation of Ser. No. 179,528, Jan. 10, 1994, abandoned.

[30] Foreign Application Priority Data

Jan. 13, 1993 [IT] Italy .................................. MI93A0029

[51] Int. Cl.$^6$ .............................. C07H 1/06; C07H 11/04

[52] U.S. Cl. ............................................ 536/117; 536/124

[58] Field of Search ........................................ 536/117, 124

[56] References Cited

U.S. PATENT DOCUMENTS 3,066,135  11/1962  Baruchello .............................. 536/117

FOREIGN PATENT DOCUMENTS 47-31932  11/1972  Japan .

*Primary Examiner*—John Kight
*Assistant Examiner*—Everett White
*Attorney, Agent, or Firm*—Notaro & Michalos

[57] ABSTRACT

A process is described for preparing octahydro trisodium salt of fructose 1,6-diphosphate starting from an aqueous solution at an acid pH of D-fructose 1,6-diphosphate, to which a suitable amount of acetone is added. The reactive mixture is crystallized and filtered to obtain the desired product, which is finally dried.

3 Claims, No Drawings

PROCESS FOR OBTAINING OCTAHYDRO TRISODIUM SALT OF FRUCTOSE 1,6-DIPHOSPHATE (FDPNA3H*8H2O) IN CRYSTALLINE FORM

This application is a continuation of application Ser. No. 08/179,528, filed Jan. 10, 1994, now abandoned.

FIELD AND BACKGROUND OF THE INVENTION

The present invention relates to a new process for obtaining octahydro trisodium salt of fructose 1,6-diphosphate in a crystalline form by using aqueous solution of FdP.

Fructose 1,6-diphosphate was isolated by Young for the first time in 1909, and actually it is widely used as a drug for the treatment of many pathological diseases. It is usually produced as sodium salt in an amorphous form, and as such it is extremely hygroscopic and deliquescent in the air. The difficulties arising during the storing and the carrying of the product, and in the preparation of pharmaceutical compositions from the produce are caused by such properties.

In DE 2,061,731 the crystalline octahydro form of trisodium salt of fructose 1,6-diphosphate (FdPNa3H*8H2O), obtained by crystallization of a hydroalcolic solution of FdP is described. Such a form, compared to the amorphous one, is not hygroscopic and it is remarkably more stable. Although effective, the process as above mentioned involves the consumption of a great amount of ethylic alcohol, the recovery of which from the mother waters is difficult because of the chemical-physical properties of the hydroalcolic mixtures. Moreover this process involves the use of large volumes of hydroalcolic solution for unity of products, thus causing the lost of one part of the product (from 4 to 9%), that remains in solution in the mother waters. Moreover, the special fiscal condition to which alcohols are subject inevitably raise the costs for industrial production.

SUMMARY OF THE INVENTION

By the present invention it was surprisingly found that the crystallization of octahydro trisodium salt of fructose 1,6-diphosphate occurs even from water/acetone mixtures, with excellent results as concernes yields and quality of the obtained products. Much a result is particularly unexpected if it is considered that the use of omologous alcohols to ethanol (methanol, n-propanol, isopropanol) leads to unsatisfactory results as already reported in the mentioned document DE 2,061,731.

Moreover the process described in the present invention has the remarkable economical advantage of an easy and almost quantitative recovery of acetone by a simple distillation of the process mother waters.

Thus this solvent can be used in producing a further batch of product without a remarkable deterioration of its quality and without any lowering of the yield.

Moreover, the process of the present invention remarkably reduces the product amount that is lost in the mother waters. This amount is from 0.2 to 2% of the product used at the beginning. In the present invention finally, a further advantage is that of being able to use less volume per unit of obtained product. This can be obtained by the fact that the process herein described is applied to a solution having up to 20% (w/v) of fructose 1,6-diphosphate.

DESCRIPTION OF THE PREFERRED EMBODIMENT

The process described in the present invention provides for regulating a fructose 1,6-diphosphate aqueous solution as a first step: obtaining a pH of from 5.5 and 6.3, preferably from 5.8 and 6.0 and at a temperature of 0° to 15° C.; the solution so obtained will be able to have a content of FdP of from 70 and 200 mg/ml, and will be added to a first share of acetone to reach a persistent dull mixture; said mixture is then poured into a further amount of acetone suitably cooled and under stirring.

The acetone added in all is equal in amount to from two to three times the starting aqueous solution.

After a long time for stirring, the suspension is kept at rest and at low temperature until crystallization takes place. The solid thus obtained is filtered, washed by acetone and dried. Thus obtaining a constant weight. Drying takes place at lower temperature of about 30° C. and without the aid of dehydrating agents in order to avoid the loss of crystallization water.

The following example particularly describes the invention without limiting it.

EXAMPLE

A solution of FdP sodium salt (1.4 l, 111 mg/ml in FdPH4, pH 5.3) is adjusted to pH=5.85 by about 120 ml of 2N NaOH and maintaining a temperature lower than 10° C. 500 ml of acetone cooled to 5° C. is added, always with the mixture kept at a temperature lower than 10° C., obtaining the persistent dull of the solution. The mixture is then poured (at a rate of about 70 ml/min) into 3.6 l of acetone cooled at 2° C. and kept under vigorous stirring. During the addition the temperature the mixture does not go above 3° C. After 12 hours of stirring, the solution is kept on for a further 10 hours rest at 2° C. The suspension is thus filtered under reduced pressure and the white solid is washed by acetone (2×80 ml). Then it is dried under 10–20 mbar at room temperature in the presence of activated carbon to a constant weight, thus obtaining 228.8 g of product (chemical yield 90% ). The mother waters (total volume 5.2 l) are limpid and colourless, and can be distilled again under atmospheric pressure for recovering acetone (3.3–3.4 l, Tdist.=58°–62° C. title 96–97%).

The product analysis gives remarkable values by formula $C_6H_{11}O_{12}P_2Na_3 \cdot 8H_2O$ (M.W. 550.18):

|  | Found % | Calculated % |
| --- | --- | --- |
| FdPH4 | 61.2 | 61.8 |
| Na | 12.9 | 12.5 |
| H2O | 25.4 | 26.2 |
| P inorg. | 0.13 | |
| Fructose-6P | 0.36 | |
| Glucose-6P | 0.13 | |

We claim:
1. A process for producing trisodium salt of fructose 1,6-diphosphate octahydrate in a crystalline form comprising: adjusting an aqueous solution of fructose 1,6-diphosphate to a pH of from 5.5 to 6.3 using NaOH at a temperature of from 0° to 15° C., thus obtaining a concentration of fructose 1,6-diphosphate of from 70 to 200 mg/ml; mixing the solution with a total volume of acetone equal to 2.7 to 3 times the volume of the starting aqueous solution to form a reaction mixture; allowing the reaction mixture to crystallize, the temperature of the mixture not being over 10° C. during the mixing step and up to the end of the crystallization step; filtering the crystallized reaction mixture to isolate the product and then drying the product.

2. A process according to claim 1, wherein the aqueous solution of fructose 1,6-diphosphate is adjusted to a pH of from 5.8 to 6.0.

3. A process according to claim 1, wherein, after adding the NaOH, the fructose 1,6-diphosphate has a concentration of about 111 mg/ml in aqueous solution.

* * * * *